(12) United States Patent
Makino et al.

(10) Patent No.: US 7,037,536 B2
(45) Date of Patent: May 2, 2006

(54) α-AMYLASE ACTIVITY INHIBITORS

(75) Inventors: Takashi Makino, Tokyo (JP); Ritsuo Aiyama, Tokyo (JP); Yoriko Deguchi, Tokyo (JP); Masaaki Watanuki, Tokyo (JP); Masako Nakazawa, Tokyo (JP); Harumi Mizukoshi, Tokyo (JP); Masato Nagaoka, Tokyo (JP); Katsuhisa Harada, Tokyo (JP); Kuniko Osada, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 182 days.

(21) Appl. No.: 10/220,280

(22) PCT Filed: Mar. 9, 2001

(86) PCT No.: PCT/JP01/01857

§ 371 (c)(1),
(2), (4) Date: Nov. 14, 2002

(87) PCT Pub. No.: WO01/66714

PCT Pub. Date: Sep. 13, 2001

(65) Prior Publication Data
US 2003/0124208 A1    Jul. 3, 2003

(30) Foreign Application Priority Data
Mar. 10, 2000  (JP) ............................ 2000-066896

(51) Int. Cl.
*A61K 35/78* (2006.01)

(52) U.S. Cl. ...................................... 424/769; 424/725

(58) Field of Classification Search ................ 424/725, 424/769
See application file for complete search history.

(56) References Cited

U.S. PATENT DOCUMENTS 4,008,339 A * 2/1977 Matsuda et al. ......... 426/330.4
(Continued)

FOREIGN PATENT DOCUMENTS

EP            423419         4/1991
(Continued)

OTHER PUBLICATIONS

Yoriko Deguchi et al.; "Guava ha nessui chuushitsubutsu no db/db mouse ni okeru kou tounyoubyou kouka oyobi hito inyou shiken ni yoru shokugo kettouchi joushou yokusei kouka" Nippon Nougei Kagaku Gakkaishi, vol. 72, No. 8, pp. 923-931, 1998, English Abstract.

(Continued)

*Primary Examiner*—Susan Coe
*Assistant Examiner*—S. B. McCormick-Ewoldt
(74) *Attorney, Agent, or Firm*—Oblon, Spivak, McClelland, Maier & Neustadt, P.C.

(57) ABSTRACT

The present invention relates to an α-amylase activity inhibitor, and to food and beverages comprising the α-amylase activity inhibitor. The α-amylase activity inhibitor of the present invention exhibits remarkably excellent α-amylase inhibitory activity as compared with guava extract. Accordingly, food and beverages containing the α-amylase activity inhibitor are diet food and beverages suitable for people of high blood-sugar level or hyderlipidemia.

8 Claims, 2 Drawing Sheets

U.S. PATENT DOCUMENTS 5,891,905 A * 4/1999 Romanczyk et al. ....... 514/449
5,912,363 A * 6/1999 Nafisi-Movaghar et al. 549/399
5,989,557 A * 11/1999 Bombardelli et al. ....... 424/729

FOREIGN PATENT DOCUMENTS

| JP | 60-54665 | | 3/1985 |
|---|---|---|---|
| JP | 7-59539 | | 3/1995 |
| JP | 7-59539 A | * | 3/1995 |
| JP | 9-84565 | | 3/1997 |
| JP | 09-084565 | * | 3/1997 |
| JP | 10202002 A | * | 8/1998 |

OTHER PUBLICATIONS

Masako Nakazawa, et al., "Assay method for α-amylase inhibitors in the "*Psidium guajava* L" tea, " Chromatography, vol. 21, No. 2, pp. 155-156, 2000.

* cited by examiner

α-AMYLASE ACTIVITY INHIBITORS

BACKGROUND OF THE INVENTION

1. Field of the Invention

The present invention relates to an α-amylase activity inhibitor containing as an active component polyphenols originating from guava (*Psidium guajava* Linn.) (hereinafter also called "guava polyphenols"), and to food and beverages containing the inhibitor.

2. Discussion of the Background

Recently, consumers have been keenly conscious of limiting calorie ingestion, because excessive calorie ingestion is a primary cause of adults' diseases attributable to unhealthy habits. However, if there existed substances that could inhibit, or suppress, conversion of ingested food into energy in the living body, such substances would be useful for people in need of dieting, because the substances would allow people to avoid having to reduce their food intake. In particular, inhibiting digestion of carbohydrates led by starch is considered effective for the prevention and therapy of obesity, and therefore, in recent years, substances that inhibit the activity of α-amylase, a digestive enzyme for starch, have become of interest.

Guava is a shrub originating in Central America, and its fruit, roots, and leaves have been used as folk remedies for the treatment of diabetes and diarrhea. According to recent studies, an extract obtained by extracting guava leaves with water or a hydrophilic solvent inhibits α-amylase activity. Japanese Patent Publication (kokoku) No. 60-36746 discloses that the extract can be used as an ingredient of health-promoting beverages, and Japanese Patent Application Laid-Open (kokai) No. 7-59539 discloses that the extract can be used as an ingredient of diet food and beverages.

However, conventional guava extracts also contain sesquiterpene, tannin, and other components, and moreover, their α-amylase inhibitory activity is not necessarily satisfactory for the purpose of achieving desired dieting effect.

Accordingly, an object of the present invention is to isolate from a guava extract a component that exhibits particularly remarkable α-amylase inhibitory activity and thus promises to provide a more effective dieting effect. Another object of the present invention is to provide food and beverages containing the component.

DISCLOSURE OF THE INVENTION

Figure 1:
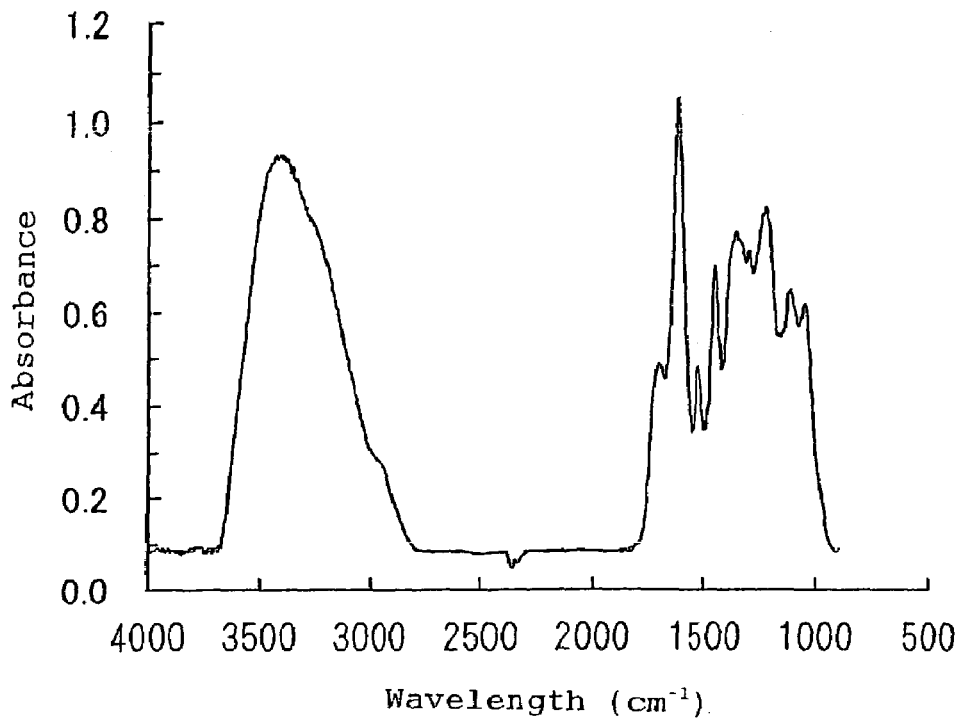
FIG. 1 is a representation of the infrared absorption spectra of guava polyphenols.

In view of the foregoing, the present inventors have performed extensive studies on high-molecular components of a guava extract, and have found that a specific class of polyphenols obtained through a process as defined in the present invention exhibits high α-amylase inhibitory activity. Briefly, according to the process of the present invention, an aqueous extract of guava leaves or guava fruit is subjected to ultrafiltration, and fractions having a molecular weight of 5,000 or more are subjected to fractionation by means of specific hydrophobic chromatography. The present invention has been accomplished on the basis of this finding.

Accordingly, the present invention provides an α-amylase activity inhibitor comprising, as an effective component, polyphenols obtained through the following process: guava leaves and/or guava fruit are subjected to extraction with one or more solvents selected from among water and hydrophilic solvents; the resultant extract is subjected to ultrafiltration, to thereby remove substances having a molecular weight of less than 5,000; the remaining fraction is applied to the butyl support hydrophobic chromatography column, and elution is carried out by use of an aqueous solution of sodium dihydrogenphosphate (0.02 mol/L) and an aqueous solution of sodium phosphate (0.02 mol/L) (flow rate: 1 mL/minute) under a pH gradient between the two solutions; and there is recovered a fraction of the eluted substance, which fraction corresponds to the third single peak of an elution curve obtained when the absorbance of the substance is measured at 260 nm.

The present invention also provides an α-amylase activity inhibitor comprising, as an effective component polyphenols having the following physicochemical properties:

(a) containing carbon (49.6%), hydrogen (4.6%), and nitrogen (0.6%);

(b) having a molecular weight of 5,000–100,000;

(c) exhibiting strong infrared absorption near 3,428 $cm^{-1}$, 1,705 $cm^{-1}$, 1,615 $cm^{-1}$, and 1,220 $cm^{-1}$;

(d) exhibiting solid carbon nuclear magnetic resonance spectra corresponding to a sugar signal (in the vicinity of 76 ppm), an aromatic signal (in the vicinity of 115.0 ppm), a phenol signal (in the vicinity of 144 and 156 ppm), and an ester carbonyl signal (in the vicinity of 168 ppm); and (e) exhibiting a single peak at around 10 minutes when subjected to liquid chromatography under the following conditions:

column: a column filled with hard synthetic polymer-type reversed phase distribution gel to which butyl groups are chemically bonded (model: Shodex Asahipak C4P-50 4D (product of Showa Denko), inner diameter: 4.6 mm, length: 150 mm), or a column similar to this column);

flow rate: 1.5 mL/minute;

column temperature: a specific temperature around 40° C.;

detector: UV absorptiometer (wavelength: 260 nm);

mobile phase:

solution A: a solution mixture of acetonitrile containing $NaH_2PO_4$ (0.02 mol/L) and water (15:85 (v/v)) (pH=4.6); and solution B: a solution mixture of acetonitrile containing $Na_3PO_4$ (0.02 mol/L) and water (15:85 (v/v)) (pH=11.4); and analysis method: a step gradient analysis performed on the basis of the data listed in the following Table.

TABLE 1

| Analysis time (min) | Solution A (%) | Solution B (%) |
| --- | --- | --- |
| 0 (to 4) | 100 | 0 |
| 4 (to 8) | 65 | 35 |
| 8 (to 12) | 0 | 100 |
| 12 (to 20) | 100 | 0 |

The present invention also provides food and beverages containing the α-amylase activity inhibitor.

The present invention also provides use of the for producing diet food and beverages.

The present invention also provides a dieting method comprising intake of the food and beverages.

BEST MODE FOR CARRYING OUT THE INVENTION

The polyphenols of the present invention can be produced through the below-described steps 1 through 3.

1) Step 1

Guava leaves and/or guava fruit are subjected to extraction with one or more solvents selected from among water and hydrophilic solvents, to thereby obtain a guava extract.

The guava employed in the present invention is *Psidium guajava* Linn., and the region in which the guava is grown is not particularly limited. In the present invention, guava which occurs naturally or is cultivated in the tropical or subtropical zones of Southeast Asia, South Asia, South America, or North America may be employed. In the present invention, leaves or fruit of the guava are employed. Raw guava, semi-dried guava, or dried guava may be employed, but preferably, dried guava leaves in particular are employed. When guava fruit is employed, unripe fruit is preferably employed. Such guava leaves or fruit, serving as raw material, are preferably pulverized before use. For example, when guava leaves are used, the leaves are preferably cut into pieces having a size of about 3–5 mm. Meanwhile, guava which is dried and then roasted may be used in order to improve taste.

One or more solvents selected from among water and hydrophilic solvents are used as the extraction solvent. Examples of the hydrophilic solvents include methanol, ethanol, n-propyl alcohol, acetone, and propylene glycol. These solvents may be used in combination with two or more species. Alternatively, these solvents may be mixed with water at an arbitrary ratio for use in the form of water-containing solvent. In order to facilitate operation and enhance safety, water is most preferably employed as the extraction solvent.

The amount of the extraction solvent employed is not particularly limited. However, when guava leaves are employed, the weight ratio of the leaves to the solvent is preferably 1:20. When unripe guava fruit is employed, the weight of the solvent is preferably about 10 times that of the fruit.

When guava leaves are subjected to extraction, extraction conditions vary in accordance with the type of the solvent which is employed. When water is used as the solvent, extraction is carried out at 50–100° C., preferably 80–100° C., for 5–60 minutes, preferably 5–25 minutes.

When unripe guava fruit is used, extraction is preferably carried out at 60–100° C. for 10–60 minutes.

When extraction is carried out, an alkali such as sodium bicarbonate may be added to the extraction solvent, to thereby increase the pH of the solvent. Alternatively, a dilute mineral acid (e.g., dilute hydrochloric acid) or an organic acid (e.g., succinic acid, citric acid, lactic acid, malic acid, or tartaric acid) may be added to the extraction solvent, bringing the solvent to a weakly acidic condition.

After completion of the extraction step, preferably, the resultant extract is cooled and then subjected to centrifugation, removing impurities from the extract. The thus-obtained guava extract may be concentrated or diluted so as to attain an appropriate concentration.

2) Step 2

The guava extract obtained through step 1 is subjected to ultrafiltration, to thereby remove low-molecular-weight substances having a molecular weight of less than 5,000.

For ultrafiltration of the guava extract, there may be used a method employing a press-type filtration apparatus, dialysis, centrifugation, etc. These methods and techniques may be used in combination.

When dialysis is carried out, the guava extract is placed in a dialysis tube formed of a semipermeable membrane which can be permeated by a substance having a molecular weight of less than 5,000, the membrane being formed from a material such as cellulose ester or cellophane. Subsequently, the guava extract is dialyzed against water or a dilute buffer (hereinafter referred to as dialysate) for one to seven days, preferably two to three days, while the dialysate is periodically exchanged with a fresh dialysate or water is caused to flow constantly. Through the above procedure, the low-molecular-weight substances are diffused into the dialysate for removal of the substances from the guava extract.

3) Step 3

A fraction having a molecular weight of 5,000 or more obtained through step 2 is subjected to butyl support hydrophobic chromatography. The material was applied to the column and the elution (flow rate: 1 mL/min) of the sample was accomplished with the pH gradient from sodium dihydrogenphosphate solution (0.02 mol/L) to sodium phosphate solution (0.02 mol/L).

The filler employed in hydrophobic chromatography as a stationary phase is not particularly limited, so long as the filler carries butyl groups as functional groups and has satisfactory mechanical strength. Examples of the filler include polystyrene, carboxylated polystyrene, polymethyl acrylate, and cellulose derivatives.

A sodium dihydrogenphosphate aqueous solution (0.02 mol/L) and a sodium phosphate aqueous solution (0.02 mol/L) are employed as a mobile phase, and elution is carried out under a concentration gradient between the two solutions.

The solvents are passed through the column (flow rate: 1 mL/min), and the separation pattern of the eluted substance is obtained by measuring the absorbance of the eluted substance at 260 nm. Subsequently, a fraction which corresponds to the third single peak of the pattern is recovered, and the thus-recovered fraction is dried in vacuum or freeze-dried, to thereby obtain the polyphenols of the present invention.

The physicochemical properties of the water-soluble fraction obtained as described above will next be described.

Elementary Analysis

Elementary analysis was carried out through a customary method. The results are shown in Table 2.

TABLE 2

Results of elementary analysis

| Element | Found (%) |
| --- | --- |
| Carbon (C) | 49.6 |
| Hydrogen (H) | 4.6 |
| Nitrogen (N) | 0.6 |

In view of the very low nitrogen content, the fraction is considered to contain no protein.

Molecular Weight

The molecular weight of the fraction was determined through GPC-HPLC by use of a multi-angle light-scattering detector according to a customary method. The molecular weight of the fraction was found to be 5,000–100,000, and the average molecular weight was found to be 70,000.

Component Analysis

The sugar content of the fraction was obtained as follows: a sample was heated and decomposed in 4 mol/L-trifluoroacetic acid at 100° C. for two hours; an aldonic nitrile acetate derivative was formed according to a customary method; and then the sugar content was calculated through gas chromatography analysis. The results: glucose (2.1%), arabinose (2.0%), galactose (1.3%), mannose (0.4%), rhamnose (0.3%), and xylose (0.3%).

Gallic Acid Content, Ellagic Acid Content, and Proanthocyanidin Content

The gallic acid content and the ellagic acid content of the sample were determined by heating the sample in a butanol-hydrochloric acid mixture (95:5 v/v) containing ammonium iron(III) sulfate, at 100° C. for 24 hours to thereby decompose the sample; and analyzing the decomposed sample through HPLC. The gallic acid content and the ellagic acid content were found to be 0.6% and 5.2%, respectively. The proanthocyanidin content of the sample was determined by heating the sample by use of the same reagent at 95° C. for 40 minutes to thereby decompose the sample, and calculating the content from absorbance of the decomposed solution. The proanthocyanidin content as reduced to cyanidin was found to be 6.8%.

Infrared Absorption Spectrum

The sample was sandwiched between $BaF_2$ crystals, and rolled under pressure. Measurement was carried out through the transmission method. In the obtained IR absorption spectrum, strong absorption peaks attributed to the fraction were confirmed at approximately 3428 $cm^{-1}$, 1705 $cm^{-1}$, 1615 $cm^{-1}$, and 1220 $cm^{-1}$. The IR absorption spectrum is shown in FIG. 1.

Solid Carbon Nuclear Magnetic Resonance Spectrum (Solid $^{13}$C-NMR)

Figure 2:
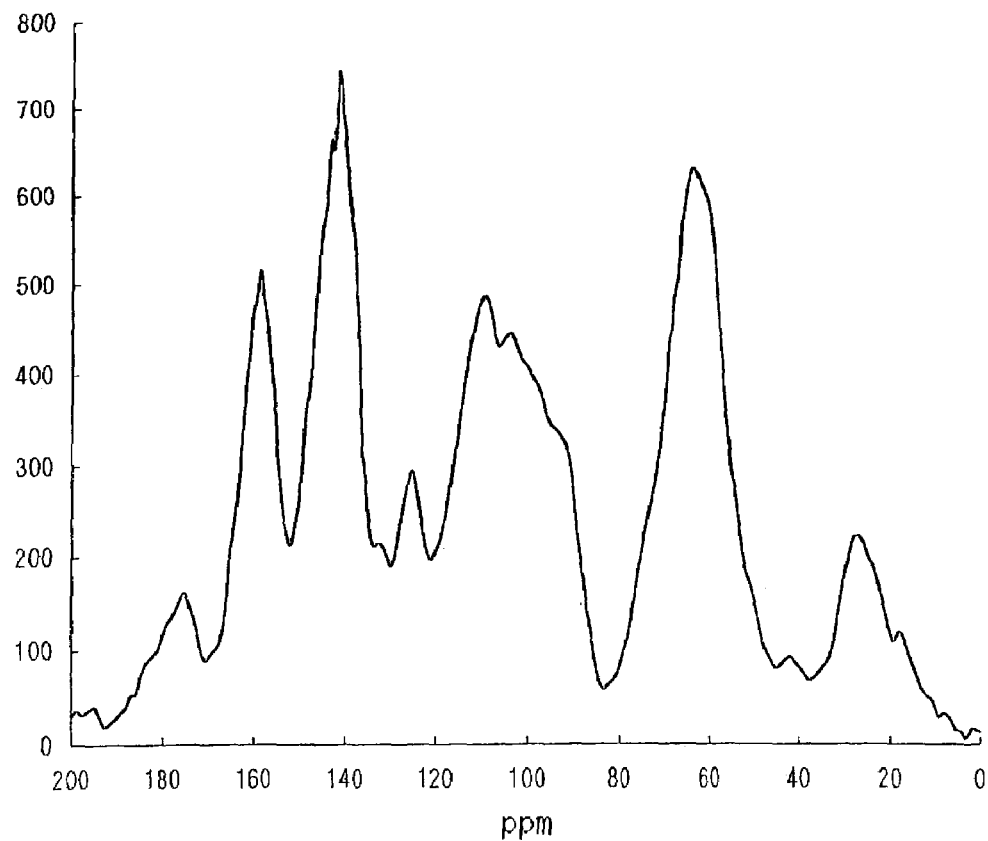
FIG. 2 is a representation of the cross-polarization magic-angle spinning (CP-MAS) spectra of guava polypenols.

A customary method, specifically, cross-polarization magic-angle spinning (CP-MAS) was used. In the obtained CP-MAS spectrum, signals attributed to substances such as sugar, aromatics, phenol, and ester carbonyl were observed. The spectrum confirmed that the fraction was formed of polyphenols predominantly containing a group of ellagitannins. The CP-MAS spectrum is shown in FIG. 2.

The aforementioned guava polyphenols exhibit, as shown in the below-described Examples, an excellent α-amylase inhibitory activity and also an α-glucosidase inhibitory activity. Accordingly, when food into which the polyphenols have been incorporated is ingested, degradation of starch into dextrin and maltose is effectively prevented, and further, degradation of disaccharides (maltose, isomaltose, sucrose) into glucose is also prevented. Thus, incorporation of the polyphenols can provide food and beverages having an effect of preventing blood-sugar elevation and an anti-obesity effect.

Examples of forms of the food and beverages according to the present invention include solid food, semi-liquid food, gel-form food, and beverages. Specific examples include tablets, encapsulated products, and granules; confectioneries such as cookies, jellies, and snack food; granulated condiments, bread, and noodles; and beverages such as refreshing beverages, juice, and beverages prepared by use of lactic acid bacteria.

In addition to the polyphenols of the present invention, a variety of materials which are typically added to food may also be incorporated into the aforementioned food and beverages. Specific examples of the materials include sugar alcohols such as glucose, sucrose, fructose, sorbitol, xylitol, erythritol, lactitol, and palatinit; emulsifiers such as sucrose fatty acid esters, polyglycerin fatty acid esters, and lecithin; and stabilizers such as pectin, carboxymethyl cellulose, aqueous soybean polysaccharides, gellan gum, gum arabic, xanthan gum, carrageenin, and guar gum. Other examples of materials which can be incorporated include vitamins such as vitamin A, B vitamins, vitamin C, and vitamin E; mineral components such as calcium lactate, calcium gluconate, calcium pantothenate, magnesium compounds, and zinc compounds; and herb extract.

When the polyphenols of the present invention are incorporated into food and beverages, the total amount of the polyphenols, which may vary depending on the form of food and beverages, is preferably 0.005–0.5 wt. %. The amount of such food and beverages to be ingested per day is preferably 5–500 mg as reduced to the polyphenols, particularly preferably 10–100 mg.

EXAMPLES

The present invention will next be described in more detail by way of examples, which should not be construed as limiting the invention thereto.

Example 1

Preparation of Guava Extract (1) Guava leaves (produced in the People's Republic of China, Kuanhsi) were dried, roasted at 121° C. for 15 minutes, and minutely cut into pieces of about 5 mm. The thus-obtained broken leaves (100 kg) were immersed in hot water (80° C., 2000 kg), to thereby effect extraction for 25 minutes. The resultant extract was cooled to 30° C. or lower, and centrifuged at 1500 rpm for 10 minutes so as to clear the solution, thereby yielding guava leaf extract.

(2) Unripe guava fruit extract was prepared by subjecting unripe guava fruit (1 part by weight) to extraction by use of a solvent (approximately 10 parts by weight) at 90° C. for 25 minutes.

(3) The unripe guava fruit extract was added to the thus-obtained guava leave extract in an amount of approximately 0.1–0.2%, thereby preparing guava extract.

Example 2

Preparation of Guava Polyphenols

Figure 3:
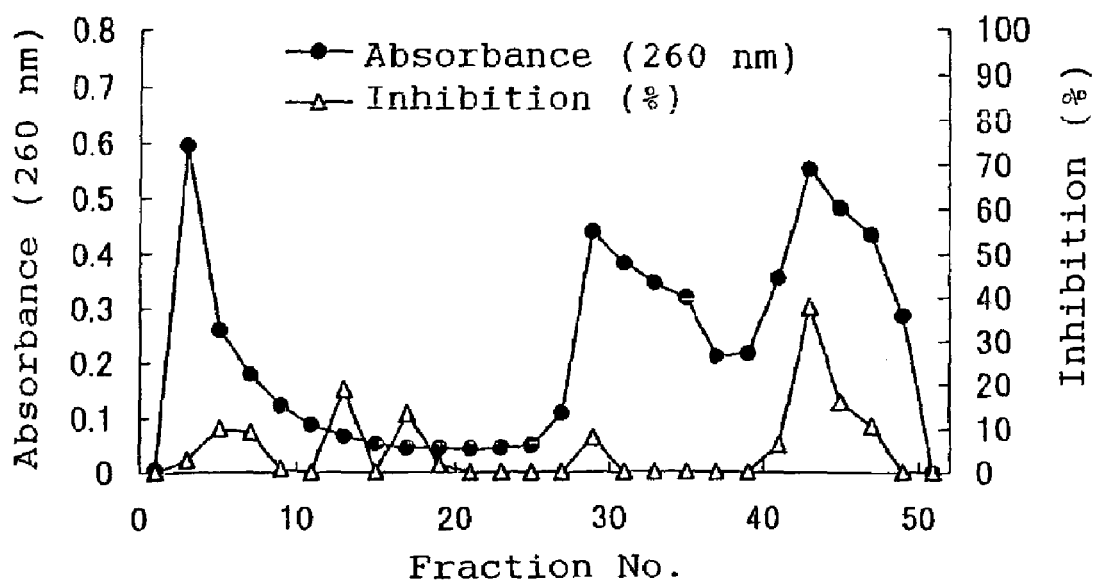
FIG. 3 is a representation of the elution curve of purified guava polyphenols.

The guava extract which had been prepared in Example 1 was filtered by means of an ultrafilter (for fractionating molecular weight of 5000), to thereby obtain a fraction of molecular weight of 5000 or more. The thus-obtained fraction was dialyzed against a dialysis membrane (for fractionating molecular weight of 6000–8000), and the separated inner liquid was freeze-dried, to thereby prepare crude polyphenols. The crude polyphenols were dissolved in a 0.02 mol/L aqueous solution of sodium dihydrogenphosphate, and the resultant solution was purified by means of hydrophobic chromatography (macro-prep column containing a butyl-group-linked filler). Specifically, after the filler was washed with a 0.02 mol/L aqueous solution of sodium dihydrogenphosphate in a volume twice the volume of the column, elution was carried out by use of a mixture, in a volume twice the volume of the column, containing a 0.02 mol/L aqueous solution of sodium dihydrogenphosphate and a 0.02 mol/L aqueous solution of trisodium phosphate under a concentration gradient (i.e., proportional change in concentration) between the two solution. Subsequently, a 0.02 mol/L aqueous solution of trisodium phosphate was applied to the column. The absorbance of the remaining fraction was measured at 260 nm, to thereby draw an elution curve, and amylase inhibitory activity was investigated (FIG. 3). As is clear from the curves in FIG. 3, the final single peak of elution overlapped the inhibitory activity peak. A fraction corresponding to that single peak were collected and subjected to electrodialysis, followed by freeze-drying, to thereby obtain a product serving as purified guava polyphenols.

Figure 4:
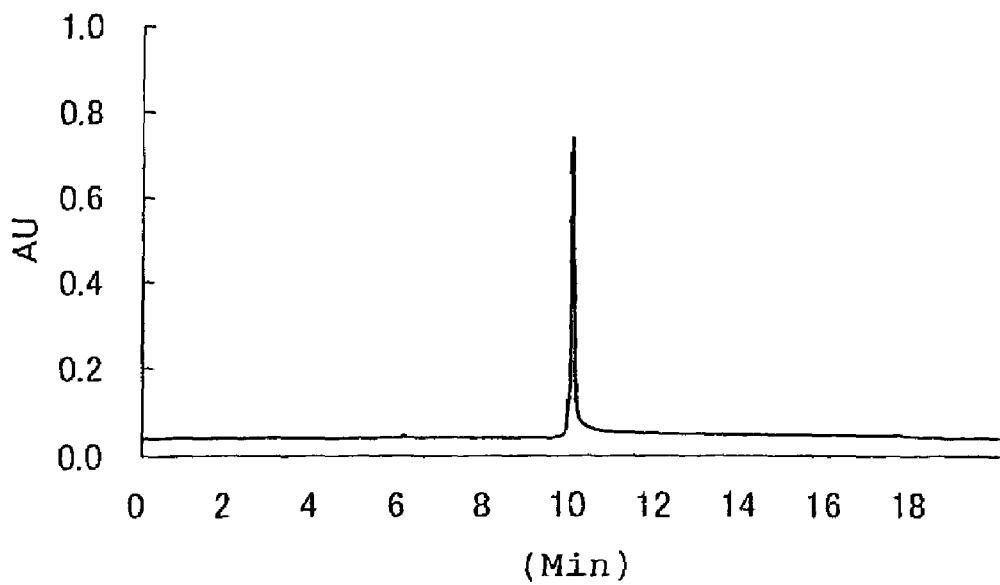
FIG. 4 is a representation of results obtained by the liquid chromatography analysis of guava polyphenols.

The thus-obtained purified guava polyphenols were chromatographically analyzed under the aforementioned measurement conditions (e). The results are shown in FIG. 4. As is clear from FIG. 4, the purified guava polyphenols of the present invention exhibit a single peak in the chromatogram measured under the above conditions.

Example 3

α-Amylase Inhibitory Activity

The effects, on α-amylase, of the guava extract and the purified guava polyphenols obtained in Examples 1 and 2, respectively, were investigated.

α-Amylase inhibitory activity was measured through a customary method. Specifically, α-amylase derived from pig pancreatic juice was mixed with a 0.02 M sodium phosphate buffer (pH 6.5), to thereby prepare an amylase solution. A substrate solution was prepared from 8% soluble starch and a 0.08 M sodium phosphate buffer (pH 6.5). Mixtures of the enzyme, substrate solution, and a test solution, or a mixture of the enzyme, substrate solution, and water serving as a control were allowed to react at 37° C. for seven minutes. The reaction was terminated at 100° C. Formed maltose was determined through HPLC by use of arabinose as an internal standard substance. The inhibitory activity was calculated by the following equation. The results are shown in Table 3.

Inhibitory activity (%)={1−(amount of formed maltose in test sample)/(amount of formed maltose in control sample)}×100

TABLE 3

| Test samples | Concentration (mg/ml) | Amylase inhibition (%) |
| --- | --- | --- |
| guava extract | 0.80 | 46 |
| purified guava polyphenols | 0.79 | 74 |

As shown in Table 3, the purified guava polyphenols of the present invention exhibited higher (approximately 30% higher) inhibitory activity as compared with guava extract.

Example 4

α-Glucosidase Inhibitory Activity

The effects, on maltase—a type of α-glucosidase—of the guava extract and the purified guava polyphenols obtained in Examples 1 and 2, respectively, were investigated.

Maltase inhibitory activity was measured through a customary method. Specifically, a crude maltase solution was prepared by homogenizing rat intestinal acetone powder (SIGMA) with a 56 mM maleate buffer (pH 6.0) in an amount nine times the powder, and collecting the centrifugal supernatant. A substrate solution was prepared by use of a 224 mM maleate buffer (pH 6.0) such that the final maltose concentration reached 1%. Mixtures of the enzyme, substrate solution, and a test solution, or a mixture of the enzyme, substrate solution, and water serving as a control were allowed to react at 37° C. for five minutes. The reaction was terminated at 100° C. Formed glucose was determined through HPLC by use of arabinose as an internal standard substance. The inhibitory activity was calculated by the following equation. The results are shown in Table 4.

Inhibitory activity (%)={1−(amount of formed glucose in test sample)/(amount of formed glucose in control sample)}×100

TABLE 4

| Test sample | Concentration (mg/ml) | Maltase inhibition (%) |
| --- | --- | --- |
| guava extract | 1.5 | 78.0 |
| purified guava polyphenols | 1.5 | 84.9 |

Example 5

By use of the purified guava polyphenols which had been prepared in Example 2, bread was made on the basis of the following formulation.

|  |  | (parts by weight) |
| --- | --- | --- |
| Formulation: | wheat flour | 52 |
|  | refined sugar | 3 |
|  | condensed milk | 4 |
|  | unsalted butter | 3 |
|  | egg | 3 |
|  | refined salt | 1 |
|  | fresh yeast | 1.5 |
|  | Water | 31.5 |
|  | guava polyphenols | 1 |

After baking, the bread had a characteristic herbal flavor and good taste, and was comparable with the taste of bread products conventionally available on the market.

INDUSTRIAL APPLICABILITY

The α-amylase activity inhibitor of the present invention exhibits remarkably excellent α-amylase inhibitory activity as compared with guava extract, and also exhibits an α-glucosidase inhibitory activity. Accordingly, by incorporating the polyphenols into food and beverages, those having an effect of suppressing blood-sugar level and an anti-obesity effect can be provided. More specifically, by incorporating the polyphenols into food containing much starch such as condiment flour, noodles, bread, and cookies, diet food and beverages suitable for people of high blood-sugar level or hyderlipidemia can be provided.

What is claimed is:

1. An α-amylase activity inhibitor obtained from a process which comprises:
   extracting guava leaves and/or guava fruit with one or more solvents selected from among water and hydrophilic solvents to obtain a resultant extract;
   subjecting the resultant extract to ultrafiltration, to thereby remove substances having a molecular weight of less than 5,000 to thereby obtain a fraction;
   applying the fraction to a butyl support hydrophobic chromatography column, and
   eluting at least one substance with an aqueous solution comprising sodium dihydrogenphosphate (0.02 mol/L) and an aqueous solution comprising sodium phosphate (0.02 mol/L) (flow rate: 1 mL/minute) under a pH gradient between the two solutions; and
   recovering the said at least one eluted substance, which fraction corresponds to the third single peak of an elution curve obtained when the absorbance of the substance is measured at 260 nm.

2. The α-amylase activity inhibitor according to claim 1, wherein said inhibitor comprises polyphenols which comprise the following physicochemical properties:
   (a) containing carbon (49.6%), hydrogen (4.6%), and nitrogen (0.6%);
   (b) having a molecular weight of 5,000–100,000;
   (c) exhibiting infrared absorption peaks at about 3,428 $cm^{-1}$, 1,705 $cm^{-1}$, 1,615 $cm^{-1}$, and 1,220 $cm^{-1}$;
   (d) exhibiting solid carbon nuclear magnetic resonance spectra corresponding to a sugar signal at 76 ppm, an aromatic signal at 115.0 ppm, phenol signals at 144 and 156 ppm, and an ester carbonyl signal at 168 ppm; and
   (e) exhibiting a single peak at around 10 minutes when subjected to liquid chromatography under the following conditions:
   column: a column packed with reversed phase synthetic polymer gel having butyl groups;
   flow rate: 1.5 mL/minute;
   column temperature: a constant temperature at about 40° C.; detector: UV photometer (wavelength: 260 nm);
   mobile phase:
   solution A: a solution mixture comprising acetonitrile, $NaH_2PO_4$ (0.02 mol/L), and water (15:85 (v/v)) (pH=4.6), and
   solution B: a solution mixture comprising acetonitrile, $Na_3PO_4$ (0.02 mol/L), and water (15:85 (v/v)) (pH=11.4); and
   analysis method: a step gradient analysis performed on the basis of the data listed in the following Table

| Analysis time (min) | Solution A (%) | Solution B (%) |
| --- | --- | --- |
| 0 ~ 4 | 100 | 0 |
| 4 ~ 8 | 65 | 35 |
| 8 ~ 12 | 0 | 100 |
| 12 ~ 20 | 100 | 0. |

3. An α-amylase activity inhibitor comprising, -polyphenols having the following physicochemical properties:
   (a) containing carbon (49.6%), hydrogen (4.6%), and nitrogen (0.6%);
   (b) having a molecular weight of 5,000–100,000;
   (c) exhibiting infrared absorption peaks at about 3,428 $cm^{-1}$, 1,705 $cm^{-1}$, 1,615 $cm^{-1}$, and 1,220 $cm^{-1}$;
   (d) exhibiting solid carbon nuclear magnetic resonance spectra corresponding to a sugar signal at 76 ppm, an aromatic signal at 115.0 ppm, phenol signals at 144 and 156 ppm, and an ester carbonyl signal at 168 ppm; and
   (e) exhibiting a single peak at around 10 minutes when subjected to liquid chromatography under the following conditions:
   column: a column packed with reversed phase synthetic polymer gel having butyl groups;
   flow rate: 1.5 mL/minute;
   column temperature: a constant temperature of about 40° C.;
   detector: UV photometer (wavelength: 260 nm);
   mobile phase:
   solution A: a solution mixture comprising acetonitrile, $NaH_2PO_4$ (0.02 mol/L), and water (15:85 (v/v)) (pH=4.6), and
   solution B: a solution mixture comprising acetonitrile, $Na_3PO_4$ (0.02 mol/L), and water (15:85 (v/v)) (pH=11.4); and
   analysis method: a step gradient analysis performed on the basis of the data listed in the following Table

| Analysis time (min) | Solution A (%) | Solution B (%) |
| --- | --- | --- |
| 0 ~ 4 | 100 | 0 |
| 4 ~ 8 | 65 | 35 |
| 8 ~ 12 | 0 | 100 |
| 12 ~ 20 | 100 | 0. |

4. A composition, comprising the α-amylase activity inhibitor according to any one of claims 1 through 3, which is capable of inhibiting an α-glucosidase.

5. A food or beverage comprising the α-amylase activity inhibitor as recited in any one of claims 1 through 3.

6. A method for producing a diet food or a diet beverage, which comprises:
   adding the α-amylase inhibitor as recited in any one of claims 1 through 3 to a food or beverage.

7. A dieting method comprising consuming the food, the beverage, or both the food and beverage as recited in claim 5.

8. A food or beverage comprising the α-amylase activity inhibitor as recited in claim 4.

* * * * *